(12) United States Patent
Leisure

(10) Patent No.: US 9,669,056 B2
(45) Date of Patent: Jun. 6, 2017

(54) MICRONUTRIENT SUPPLEMENT MADE FROM COPPER METAL

(71) Applicant: Heritage Technologies, LLC, Indianapolis, IN (US)

(72) Inventor: Nicholas J. Leisure, Rushville, IN (US)

(73) Assignee: Micronutrients USA LLC, Indianapolis, IN (US)

(*) Notice: Subject to any disclaimer, the term of this patent is extended or adjusted under 35 U.S.C. 154(b) by 290 days.

(21) Appl. No.: 14/279,731

(22) Filed: May 16, 2014

(65) Prior Publication Data

US 2015/0328257 A1 Nov. 19, 2015

(51) Int. Cl.

| | |
|---|---|
| C01G 3/05 | (2006.01) |
| A61K 33/34 | (2006.01) |
| A23K 20/174 | (2016.01) |
| A23K 20/20 | (2016.01) |
| C01G 3/02 | (2006.01) |
| A23L 33/15 | (2016.01) |
| A23L 33/16 | (2016.01) |

(52) U.S. Cl.
CPC ............ *A61K 33/34* (2013.01); *A23K 20/174* (2016.05); *A23K 20/30* (2016.05); *A23L 33/15* (2016.08); *A23L 33/16* (2016.08); *C01G 3/02* (2013.01); *C01G 3/05* (2013.01)

(58) Field of Classification Search
CPC .................................. C01G 3/05; A61K 33/34
USPC ........................................ 423/493, 462, 472
See application file for complete search history.

(56) References Cited

U.S. PATENT DOCUMENTS

| | | | |
|---|---|---|---|
| 2,046,937 A | 7/1936 | Curtin | |
| 2,162,091 A | 11/1937 | Kuss et al. | |
| 3,941,818 A | 3/1976 | Abdel-Monem | |
| 4,021,569 A | 5/1977 | Abdel-Monem | |
| 4,097,271 A * | 6/1978 | Swinkels | C22B 3/10 |
| | | | 423/100 |
| 4,103,003 A | 7/1978 | Ashmead | |
| 4,546,195 A | 10/1985 | Helbig et al. | |
| 4,900,561 A | 2/1990 | Abdel-Monem | |
| 4,948,594 A | 8/1990 | Abdel-Monem | |
| 5,061,815 A | 10/1991 | Leu | |
| 5,278,329 A | 1/1994 | Anderson | |
| 5,451,414 A | 9/1995 | Steward | |
| 5,534,043 A | 7/1996 | Steward | |
| 5,583,243 A | 12/1996 | Abdel-Monem | |
| 5,698,724 A | 12/1997 | Anderson et al. | |
| 6,114,379 A | 9/2000 | Wheelwright et al. | |
| 6,265,438 B1 | 7/2001 | Steward | |
| 7,523,563 B2 | 4/2009 | Hopf | |
| 2006/0189483 A1 | 8/2006 | Hickok | |
| 2008/0113063 A1 | 5/2008 | Roper et al. | |
| 2010/0222219 A1 | 9/2010 | Lohmann et al. | |
| 2013/0064963 A1 | 3/2013 | Leisure et al. | |

FOREIGN PATENT DOCUMENTS

| | | |
|---|---|---|
| CN | 1 528 171 A1 | 9/2004 |
| CN | 1230092 C | 12/2005 |

OTHER PUBLICATIONS

Jacobson, C.A., "Encyclopedia of Chemical Reactions", vol. III, 1949, pp. 277-278,323.*
Rigg et al., "Dissolution of Copper Scrap in Hydrochloric Acid", The Canadian Journal of Chemical Engineering, vol. 49, Aug. 1971, pp. 501-505.*
Handbook of mineralogy, "Paratacamite", 2005, taken from http://www.handbookofmineralogy.org/pdfs/paratacamite.pdf.*
Qaimkhani et al., *A New Method for the Preparation of Copper Oxychloride (A Fungicide)*, J. Chem. Soc. Pak, vol. 30, No. 3, 2008.
International Search Report and Written Opinion from corresponding PCT application No. PCT/US2015/030758 dated Jul. 20, 2015 (13 pgs).
European communication containing third party observations from corresponding European application No. 15792619.7 dated Feb. 17, 2017 (1 pg).
Text book "Copper Compounds", vol. A7, p. 577 (no publication date indicated).
Anonymous "Dicopper chloride trihydroxide—Wikipedia, the free encyclopedia", Wikipedia, Jul. 29, 2013 pp. 1-10, Retrieved from the Internet: URL: http://web.archive.cor/web/20130729091400/http://en.wikipedia.org/wiki/Dicopper_chloride_trihydroxide [retrieved on Mar. 22, 2017].
European extended Search Report from corresponding European application No. 15792619.7 dated Apr. 5, 2017 (10 pgs).
P.B. Queneau et al: The U.S. Production of Copper Chemicals from Secondary and By-product Sources:, Oct. 1, 1997 (pp. 1-5) Retrieved from the Internet: URL: http://download.springer/com/static/pdf/485/art%3A10.1007%2FBF12914737.
pdf?originUrl=http://link.springer.com/article/10.1007/BF02914737&token2-exp-1490191583 acl=/static/pds/485/art%253A10.1007%252FBF02914737.
pdf?originUrl=http%3A%2F%2Flink.springer.com%2Farticle%2F10.1007%2FBF02914737*hmac=5fcd21 [retrieved on Mar. 22, 2017].

* cited by examiner

*Primary Examiner* — Ngoc-Yen Nguyen
(74) *Attorney, Agent, or Firm* — Brinks Gilson & Lione

(57) ABSTRACT

A micronutrient supplement which is made by reacting together copper metal and either hydrochloric acid and/or cupric chloride under oxidizing conditions.

9 Claims, No Drawings

MICRONUTRIENT SUPPLEMENT MADE FROM COPPER METAL

BACKGROUND

The present invention relates generally to micronutrient supplements for food or animal feeds that enhance the survivability, growth, health and/or reproductivity of humans and other animals. More specifically, the present invention is directed to method of producing a basic salt of an essential metal, which provides high bioavailability of the essential metal to humans and other animals. In particular the present application provides a method of producing micronutrients in the form of basic metal salts that uses copper metal as a starting material.

Nutrients include vitamins and some elements usually in the form of minerals or metal salts; most notably the elements include calcium, phosphorus, potassium, iron, zinc, copper, magnesium, manganese and iodine. Micronutrients are generally consumed in small amounts, i.e., less than 1 gm/day, and many essential elements have catalytic functions. While the micronutrients are often present in minute amounts, their bioavailability is essential for survival, growth, health and reproduction. Micronutrients are important for children and other young animals, particularly during their early development years when they are rapidly growing. Furthermore, many new animal breeds require additional amounts of micronutrients as their abilities to grow at a faster rate while consuming less feed has improved. This intensive growth imposes greater metabolic stresses, causing increased susceptibility to vitamin deficiencies. It is well recognized that the needed micronutrients are often not found or not found in sufficient quantities in their food or feed sources, whether these sources are naturally occurring or commercially prepared. Consequently, virtually all industrial food and feed formulations are fortified with vitamins and minerals. The cost to commercial livestock producers for supplying micronutrients to their livestock herds can be staggering.

While human and animals' needs for additional nutrients have been well documented, the availability of the micronutrients has not always met their needs. It is not sufficient to simply increase amounts of the micronutrients in the food or feed sources. This method is ineffective, wasteful and unsafe. Many of the micronutrients are not readily absorbed; the added amounts of vitamins and minerals are simply excreted without being absorbed. Excess loading of vitamins and minerals is unsafe, and in certain circumstances, excess loading can be toxic, causing severe acute and chronic harm and can even be fatal. Thus, there is a need to provide an inexpensive, readily absorbed micronutrient to decrease costs, reduce waste and to help establish a more precise control of the nutritional requirement for humans and animals.

There is a need to provide a micronutrient supplement that is readily bioavailable, storage stable and compatible with a wide variety of different vitamins. The micronutrient supplement must also be cost-efficient to produce and provide a food source for humans and animals that will increase their survivability, growth, health and/or reproductivity.

Micronutrients are commonly produced and available in the form of salts, oxides and complexes. Oxides are relatively inexpensive; however, they are not as effectively absorbed as salts and chelated forms of micronutrients.

Complexes and particularly well-defined chelated micronutrients are relatively expensive; however, they are more easily absorbed and have good bioavailability.

Examples of various micronutrients can be found in U.S. Pat. Nos. 4,021,569, 3,941,818, 5,583,243 all to Abdel-Monem, U.S. Pat. No. 4,103,003 to Ashmead, U.S. Pat. No. 4,546,195 to Helbig et al., U.S. Pat. Nos. 4,900,561, 4,948,594 both to Abdel-Monem et al. U.S. Pat. No. 5,061,815 to Leu, U.S. Pat. No. 5,278,329 to Anderson, U.S. Pat. No. 5,698,724 to Anderson et al. U.S. Pat. No. 6,114,379 to Wheelwright et al. U.S. Pat. No. 7,523,563 to Hopf and U.S. Patent Application Publication No. 2010/0222219 to Lohmann et al.

At least one of the present inventors is a co-inventor of U.S. Pat. Nos. 5,534,043, 5,451,414 and 6,265,438, and U.S. Patent Application Publication No. 2013/0064963. These patents and published patent application disclose micronutrients that are basic metal salt of the formula $M(OH)yX(2-y)/i$, and its hydrate forms, where M is metal cation, X is an anion or anionic group, and i is 1-3 depending on the valence of X.

The micronutrients disclosed in U.S. Pat. Nos. 5,534,043, 5,451,414 and 6,265,438 were originally developed from a process that used spend etchant solutions as a source of the metal cations and a crystallization process to produce a basic metal salt having a particle size of about 30 to 300 microns.

U.S. Patent Application Publication No. 2013/0064963 describes micronutrients in the form of basic metal salts that have more versatility than similar micronutrients and which have a high degree of bioavailability and which are produced by reacting a metal oxide, or metal hydroxide, or metal carbonate of an essential mineral and an acid to form a slurry with a digestible binder and forming agglomerated particles by spray drying or other means of agglomeration.

The present application provides a method of producing micronutrients in the form of basic metal salts that uses copper metal as a starting material.

Prior to the present invention at least one co-inventor of the present invention were interested in finding better ways to make essential trace minerals to be used as nutritional supplements. They discovered that a compound's chemical structure would dictate its reactivity (rate of undergoing chemical/biochemical reactions), so they initially turned their attention to the development of a manufacturing process that would consistently produce a particular crystalline structure. Eventually they developed and refined a process to produce a unique crystalline compound that is a combination of the minerals atacamite and clinoatacamite.

Later numerous animal feeding trials were conducted and it was unexpectedly discovered that the tested essential trace minerals demonstrated significant advantages over traditional copper compounds used in nutrition. U.S. Pat. No. 5,451,414 (cited above) is directed to the discovered improved way to supply copper, a critically important mineral, into animal and human diets, and a crystallization process that was developed to make a consistent polymorph of the product at all times. That original crystallization process depended on having solutions of dissolved copper as feedstocks to feed a crystallizer.

Patent Application Publication No. 2013/0064963 (cited above) describes a different production process that uses copper oxide and either hydrochloric acid or cupric chloride solution as feedstocks to produce essential trace minerals. The primary advantage of the alternate approach was that it allowed the production of a much smaller crystal particle size range which was agglomerated to improve handling properties and reduce dustiness when the product is used.

The present invention is in part the outcome of research directed at determining whether it was possible to start with elemental copper and produce the desired polymorph of crystal structure directly, without first completely dissolving the metal to make a solution to feed into a crystallizer. The present inventors were unable to find evidence that such a process was possible. Unexpectedly the present inventors were able to find conditions under which the desired reaction proceeded, and could be controlled to yield the desired product, tribasic copper chloride, with good efficiency.

Qaimkhani et al. *A New Method for the Preparation of Copper Oxychloride (A Fungicide)*, (J. Chem. Soc. Pak, Vol. 30, No. 3, 2008) discloses several methods by which a compound generally identified as copper oxychloride can be made, and in particular compares three methods that use copper wire as a reactant. In Method II Qaimkhani et al. teaches reacting copper wire with hydrochloric acid to form a dark green solution of cupric chloride ($CuCl_2$). In a second reaction the cupric chloride is neutralized with sodium hydroxide to form what is described as copper oxychloride and sodium chloride (NaCl). The need for two separate reactions in Method II is because copper will react with chloride (from the NaCl solution) to form cuprous chloride (CuCl) which forms an insoluble coating that prevents the copper from further reaction as noted by Qaimkhani et al.

The present invention provides a process for producing tribasic copper chloride ($Cu_2(OH)_3Cl$) by reacting copper metal with hydrochloric acid or cupric chloride under conditions that allow a single overall reaction to proceed without forming unwanted salts, e.g. sodium chloride. The resulting tribasic copper chloride is of a purity that allows its used as a micronutrient. The overall process uses less expensive raw materials and results in lower environmental impact than prior known processes.

BRIEF SUMMARY

According to various features, characteristics and embodiments of the present invention which will become apparent as the description thereof proceeds, the present invention provides a method of making a micronutrient supplement basic copper chloride ($Cu_2(OH)_3Cl$) from copper metal which comprises reacting together:

copper metal;
one of:
  i) hydrochloric acid or
  ii) cupric chloride; and
an oxidizing agent to form tribasic copper chloride.

The copper metal can comprise stock copper or scrap or recyclable copper,

The oxidizing agent can comprise an oxygen containing gas or oxygen which can be injected into the reaction mixture to prevent the copper metal from settling during the reaction.

The copper metal and one of hydrochloric acid and cupric chloride and oxidizing agent are reacted at a temperature of about 180° F. and stirred during the reaction.

The formed tribasic copper chloride comprises a slurry which can be spray dried or agglomerated by other means.

DETAILED DESCRIPTION OF THE DRAWINGS AND THE PRESENTLY PREFERRED EMBODIMENTS

The present invention is directed to micronutrient supplements and methods of preparing the micronutrient supplements. The micronutrient supplements of the present invention can be administered directly to humans or animals as a solid, a suspension or an admixture containing other nutrients such as vitamins, minerals, and food or animal feeds to enhance the survivability, growth, health and/or reproductivity of humans and animals. The basic salt in the micronutrient supplement includes a divalent cation of an essential metal, a pharmaceutically acceptable anion, and a hydroxyl moiety. The micronutrient supplement of the present invention provides good bioavailability of the essential metal in that it is readily absorbed or taken up in a biologically-effective amount. The micronutrient can be combined with other nutrients, particularly vitamins, to provide a premixed supplement. The premixed supplement that includes the basic salt according to the present invention can be stored for extended periods of time without significant decrease in the bioactivity of the included vitamin(s).

An essential metal is defined for the purposes of this invention as a pharmaceutically acceptable metal whose uptake by humans or other animals in a biologically effective amount increases their survivability, growth, health and/or reproductivity. The mode of action of the essential metal is not critical for the present invention. For example, the essential metal can act as a co-factor or a catalyst in a metalloenzyme or metalloprotein; it can be absorbed by a variety of tissues.

Alternatively, the essential metal or a metabolite thereof can inhibit growth of bacteria or other pathogens detrimental to the survivability, growth, health and/or reproductivity of the animal.

According to the present invention the basic metal salt, tribasic copper chloride ($Cu_2(OH)_3Cl$), includes a divalent copper cation, a hydroxyl group and a monovalent chlorine anion. In the microstructure that makes up the basic salt, the copper cation includes a hydroxyl group in its coordination sphere.

The chlorine anion of the basic metal salt is a pharmaceutically acceptable anion. Pharmaceutically acceptable anions are well known in the art. See, for example, S. M. Berge et al. J. Pharmaceutical Sciences, 66:1-19, 1977 for a listing of pharmaceutically acceptable anions, which is incorporated herein by reference.

The chlorine anion that is used in the present invention imparts significant biological effects in its own right. In general specific examples of biologically significant anions include, but are not limited to: iodide, chloride, and phosphate (phosphorus). These biologically significant anions can also be considered as micronutrients, with chlorine anion being particularly useful for purposes of the present invention. Thus, it is within the scope of the present invention to provide basic salts of essential elements that may not necessarily be considered metals such as chloride.

Basic metal salts that are used as micronutrients are generally water insoluble, but their solubility can depend upon pH. Typically, the basic metal salts have some solubility at a low pH, i.e., pH less than about 2.0 to about 0.1. In addition, certain basic metal salts dissolve in water at a high pH, typically at a pH greater than about 7.5 or 8 to about 11.

The basic reaction for producing the micronutrients according to the present invention involves reacting copper metal with hydrochloric acid or cupric chloride ($CuCl_2$) under oxidizing conditions.

The copper metal can be any type of stock copper or scrap or recyclable copper such as, but not limited to, copper rod mill scale, wire chop, copper filings, copper millings, etc. The copper provided as a powder, in granular form or chopped pieces (e.g. chopped wire), or any form, it being noted that increasing the surface area of the copper such as by reducing the particle size, will increase the reaction rate.

In laboratory bench scale testing, the necessary oxygen was supplied by adding hydrogen peroxide to the reaction mixture. In larger scale testing and commercial applications oxygen can be supplied by injecting oxygen into the reaction mixture. Any suitable conventional oxygen injection system can be used. A particularly suitable oxygen injector system developed during the course of the present invention referred to as a pipeline oxidizer is described below in reference to the working examples.

For the embodiment of the invention in which copper metal is reacted with hydrochloric acid under oxidizing conditions the overall reaction for producing tribasic copper chloride is:

$$2Cu+O_2+H_2O+HCl \rightarrow Cu_2(OH)_3Cl$$

The present inventors theorize that the overall general reaction proceeds as follows:

Copper dissolves forming cupric chloride:

$$Cu+2HCl+\tfrac{1}{2}O_2 \rightarrow CuCl_2+H_2O \quad \text{(i)}$$

Cupric chloride dissolves more Cu forming cuprous chloride:

$$CuCl_2+Cu \rightarrow 2CuCl \quad \text{(ii)}$$

Cuprous chloride is oxidized to form tribasic copper chloride and cupric chloride returns to dissolve more copper in step (ii):

$$12CuCl+3O_2+6H_2O \rightarrow 4CuCl_2+4Cu_2(OH)_3Cl \quad \text{(iii)}$$

This reaction can be carried out in a reactor in which the copper metal is added to a mixture of hydrochloric acid and water. Oxygen is added/injected into the reaction mixture and continuously added/injected throughout the reaction.

The reaction mixture is heated to and maintained at a temperature of about 180° F. To prevent metal copper from settling to the bottom of the reaction mixture a mixer of any conventional type that can inhibit material from settling in the bottom of the reactor and/or an oxygen injector that can mix/flush copper metal from the reactor bottom as discussed herein is provided and operated during the reaction.

For the embodiment of the invention in which copper metal is reacted with cupric chloride under oxidizing conditions the overall reaction for producing tribasic copper chloride is:

$$3Cu+CuCl_2+1.5O_2+3H_2O \rightarrow 2Cu_2(OH)_3Cl$$

The reaction can be carried out in a reactor in which the copper metal is added to a mixture of the cupric chloride and water. As in the reaction above, oxygen is added/injected into the reaction mixture and continuously added/injected throughout the reaction.

The reaction mixture is heated to and maintained at a temperature of about 180° F. and a mixer of any conventional type that can inhibit material from settling in the bottom of the reactor and/or an oxygen injector that can mix/flush copper metal that might otherwise settle in the bottom of the reactor as discussed herein is provided and operated during the reaction.

Either of the reactions can be conducted in a batch mode, semi-batch mode or in a continuous manner.

Each reaction produces a solid slurry of tribasic copper chloride crystals which can be spray dried or processed in any manner to recover the tribasic copper chloride crystals. According to one embodiment a digestible binder can be added to the solids slurry and the resulting slurry can be agglomerated by spray drying or other means of agglomeration to form agglomerates of the micronutrient crystals as taught in U.S. Patent Application Publication No. 2013/0064963.

The micronutrient supplements of the present invention can be admixed with other nutrients. Nutrients include both micro- and macronutrients. Examples of micronutrients include vitamins and minerals. Examples of vitamins useful for the present invention include: vitamin A, vitamin $D_3$, vitamin E (tocopherol), vitamin K (menadione), vitamin $B_{12}$ (cyanocobalamin), vitamin $B_6$, vitamin $B_1$, vitamin C (ascorbic acid), niacin, riboflavin, thiamine mononitrate, folic acid, calcium pentothenate, pyridoxine, choline chloride, biotin, known pharmaceutically acceptable derivatives of these vitamins and mixtures thereof. Examples of minerals or metal salts useful for the present invention include copper sulfate, iron sulfate, zinc oxide, manganese, iron, iodine, selenium, amino acid complexes of the trace metals and mixtures thereof. The macronutrients that can be used in the present invention include any of the common feed ingredients such as, for example, grain, seeds, grasses, meat meal, fish meal, fats and oils.

Features and characteristics of the present invention will be exemplified by the following examples which are provided as a non-limiting example for illustrative purposes only.

The following Examples include laboratory bench trials and pilot scale trials.

The laboratory bench trials were conducted in glass beakers on heated, magnetic stir plates or in some cases top mounted mixers were employed. In all cases the chemistry and recipes were similar in that copper was added to a mixture of HCl and water, at or near stoichiometric ratios to produce basic copper chloride. The mixtures were mixed and heated to about 180° F. For all the laboratory trials 30% hydrogen peroxide was used as the oxygen source. The hydrogen peroxide was added incrementally throughout the trials as needed to convert $Cu^+$ to $Cu^{++}$. The target recipe for the mixtures were designed to yield 50% by weight solids slurries of tribasic copper chloride crystals which was determined to be suitable for spray drying.

The pilot scale trials were conducted in cone bottom, fiberglass mix tanks equipped with live steam injection for temperature control. The recipes used in the pilot trials were similar to those used in the laboratory bench trials however gaseous oxygen was utilized as the oxygen source rather than hydrogen peroxide. The $O_2$ gas is more efficient both from a cost and processing standpoint. The oxidation was accomplished through a "pipeline oxidizer." This set up consisted of a pump which draws from the top of the tank (to avoid inclusion of large copper pieces) and pumps through 100' coil and then back into the bottom of the tank. Oxygen is injected inline just before the coil. Static mixers were provided at the beginning and end of the coil to provide intimate mixing of the oxygen with the liquid stream. The concept is to provide good contact and residence time under pressure to yield high oxidation efficiencies. The discharge of the pipeline oxidizer entering the bottom of the cone provided two functions: 1) Mixing/flushing action to any copper pieces that may have settled to the bottom of the cone to prevent plugging; and 2) Providing a $Cu^{++}$ rich solution to any settled copper in the bottom of the reactor to continue to drive the reaction. Also any unreacted oxygen gas has a second chance to oxidize $Cu^+$ inside the mix tank increasing oxidation efficiency.

Example 1

In this Example basic copper chloride was produced by reacting fine copper metal powder with hydrochloric acid and hydrogen peroxide according to the following reaction.

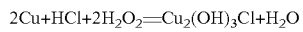

The reactants are added at or near their stoichiometry amounts. HCl was added at a slight excess to assist in driving the reaction. 61 ml of water was first added to a 250 ml beaker followed by 46 ml of 32% HCl. While mixing, 53.57 g/l of copper powder was added to the beaker. The temperature of the beaker was maintained at or near 180° F. Throughout the trial 30% hydrogen peroxide was added incrementally to convert $Cu^+$ as it formed to $Cu^{++}$. The reaction was allowed to proceed for a total of 24 hours. During the reaction time the mixture transitioned from clear to dark brown (cuprous chloride) solution to dark brown solution with white crystals of cuprous chloride, and then finally to a thick slurry of bright green crystals (tribasic copper chloride). At the end of the 24 hour period there was no visible copper present. A sample of the slurry was dried and analyzed by XRAY Diffraction to determine crystal structure. The results showed that the material was 99.1% basic copper chloride (defined as atacamite and clinoatacamite) and 0.1% cuprous chloride. The solids content of the slurry was about 50% solids, which was determined to be suitable for purposes of spray drying.

Example 2

The process and recipe for this Example were exactly the same as in Example 1 however the copper source was a bare bright, copper wire chop. The copper was of a size and density that would not allow it to be evenly dispersed through the solution as was the copper powder in Example 1. The copper remained in the bottom ⅓ of the beaker and was being moved around by the mixing action. During the trial the same transitions were observed throughout the trial as were in Example 1 however at a much slower rate. After 24 hours it was visually estimated that about 50% of the copper had been converted to basic copper chloride. After about 32 hours of reaction time the contents of the beaker had turned to the typical green color of basic copper chloride however there was still unreacted copper metal still visible on the bottom of the beaker. Analysis showed a 70% conversion of the copper into basic copper chloride.

Example 3

In this Example basic copper chloride was produced from copper rod mill scale—a byproduct from copper rod manufacturing. The copper rod mill scale was granular and included about 50 wt. % copper with a balance of cuprous oxide and cupric oxide. The copper assay on the material used was about 87.46 wt. % copper.

In this Example 70 ml of water was first added to a 250 ml beaker followed by 45.1 ml of 32% HCl. While mixing, 68.05 g/l of copper rod mill scale was added to the beaker. The temperature of the beaker was maintained at or near 180° F. Throughout the trial 30% hydrogen peroxide was added incrementally to convert $Cu^+$ as it formed to $Cu^{++}$. The reaction was allowed to proceed for a total of 24 hours. During the reaction time the mixture transitioned from clear to dark brown (cuprous chloride) solution to dark brown solution with white crystals of cuprous chloride, and then finally a thick slurry of bright green crystals (basic copper chloride). At the end of the 24 hour period there was no visible copper present. A sample of the slurry was dried and analyzed by XRAY Diffraction to determine crystal structure. The results showed that the material was 95.7% basic copper chloride (defined as atacamite and clinoatacamite) and 4.3% cuprous oxide.

Example 4

In this Example a pilot scale trial was performed to convert copper chop to basic copper chloride using cupric chloride in place of HCl. The basic copper chloride was produced by reacting cupric chloride with copper metal by the following reaction:

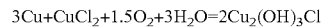

This pilot trial was performed in a 5000 gallon, cone bottom fiberglass mix tank equipped with a pipeline oxidizer as described above. The recipe was designed to yield about 11,000 lbs of basic copper chloride assuming a 100% completion of reaction.

The cupric chloride used in this trial contained 188 g/l of Cu and 1.34N free hydrochloric acid. 844 gallon of this solution was transferred to the mix tank along with 715 gallon of water. While mixing, 5229 lbs of copper wire chop was added incrementally over 12 hours at a rate of 110 lb/15 min. After the first addition of copper, the pump was started to send flow through the pipeline oxidizer. Oxygen injection into the pipeline was also started at this time. Progress was monitored by measuring total copper and density of the mixture. The reaction rate slowed dramatically after 24 hours and after 48 hours seemed to have almost completely stalled. After 48 hours of reaction a total of 77.4% of the copper had been converted to basic copper chloride.

The basic metal salts of this invention can be used to enhance the survivability, growth rate, health and/or reproductivity in humans and other animals. While not to be bound by any theory, it is thought that the basic metal salts are more readily absorbed and/or exhibit an increased bio-availability over minerals, inorganic metal salts or other nutrients containing the corresponding essential metals. It has been determined the preferred embodiments of the basic metal salts of this invention significantly reduce the growth of bacteria, thus indicating the use of preferred forms of this invention can effectively enhance the growth and health of humans and other animals. Furthermore, the preferred basic metal salts of this invention demonstrate an enhanced efficacy against certain bacteria, thereby allowing for the use of smaller amounts and/or lower concentrations of the essential metals to provide substantially equal or equal potent effects on animals.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

The invention claimed is:
1. A method of making a micronutrient supplement from copper metal which method consists of the steps of:
   a) providing as reactants:
      i) copper metal;
      ii) one of hydrochloric acid and/or cupric chloride; and
      iii) an oxidizing agent; and
   b) conducting a reaction by reacting together reactants i), ii) and iii) according to one of the following chemical equations:

i) $2Cu + HCl + 2H_2O_2 \rightarrow Cu_2(OH)_3Cl + H_2O$, ii) $3Cu + CuCl_2 + 1.5O_2 + 3H_2O \rightarrow 2Cu_2(OH)_3Cl$, and iii) $2Cu + O_2 + H_2O + HCl \rightarrow Cu_2(OH)_3Cl$, wherein the reaction of step b) produces tribasic copper chloride ($Cu_2(OH)_3Cl$) without any byproducts which would preclude use of the tribasic copper chloride as a pharmaceutically acceptable micronutrient supplement that can be added to animal feed mixtures and fed to animals.

2. A method of making a micronutrient supplement according to claim 1, wherein the copper metal comprises stock copper.

3. A method of making a micronutrient supplement according to claim 1, wherein the copper metal comprises scrap or waste copper.

4. A method of making a micronutrient supplement according to claim 1, wherein in step b) the reactants are reacted in accordance with reaction equation ii) or iii) with the copper metal and one of hydrochloric acid and cupric chloride forming a reaction mixture and the oxygen being injected into the reaction mixture.

5. A method of making a micronutrient supplement according to claim 4, wherein the injection of the oxygen inhibits the copper metal from settling during the reaction.

6. A method of making a micronutrient supplements according to claim 1, wherein the reaction in step b) is conducted at a temperature of about 180° F.

7. A method of making a micronutrient supplements according to claim 1, wherein the reaction in step b) is conducted while stirring the reactants.

8. A method of making a micronutrient supplements according to claim 1, wherein the formed tribasic copper chloride comprises a slurry.

9. A method of making a micronutrient supplements according to claim 8, wherein the slurry is spray dried.

* * * * *